(12) United States Patent
Holmberg et al.

(10) Patent No.: US 7,736,666 B2
(45) Date of Patent: Jun. 15, 2010

(54) SELF EMULSIFYING DRUG DELIVERY SYSTEM

(75) Inventors: Christina Holmberg, Södertälje (SE); Britta Siekmann, Lomma (CH)

(73) Assignee: Nicox S.A., Sophia Antipolis (FR)

( * ) Notice: Subject to any disclaimer, the term of this patent is extended or adjusted under 35 U.S.C. 154(b) by 0 days.

(21) Appl. No.: 10/221,079

(22) PCT Filed: Mar. 6, 2001

(86) PCT No.: PCT/SE01/00466

§ 371 (c)(1),
(2), (4) Date: Sep. 5, 2002

(87) PCT Pub. No.: WO01/66087

PCT Pub. Date: Sep. 13, 2001

(65) Prior Publication Data

US 2003/0077303 A1    Apr. 24, 2003

(30) Foreign Application Priority Data

Mar. 8, 2000    (SE) .................................. 0000774

(51) Int. Cl.
*A61K 9/48*    (2006.01)
*A61K 9/64*    (2006.01)
*A61K 9/127*   (2006.01)

(52) U.S. Cl. ......................... 424/456; 424/450; 424/451
(58) Field of Classification Search ................. 424/451, 424/452, 455, 456
See application file for complete search history.

(56) References Cited

U.S. PATENT DOCUMENTS

| | | | |
|---|---|---|---|
| 4,255,431 A | 3/1981 | Junggren et al. ............ 424/263 |
| 4,508,905 A | 4/1985 | Junggren et al. ............ 546/271 |
| 4,554,276 A | 11/1985 | LaMattina ................... 514/272 |
| 4,562,261 A | 12/1985 | Hirata et al. ................. 548/184 |
| 4,619,934 A | 10/1986 | Sunshine et al. ............ 514/277 |
| 4,676,984 A | 6/1987 | Wu et al. ..................... 424/157 |
| 4,704,278 A | 11/1987 | Wu et al. ..................... 424/157 |
| 4,757,060 A | 7/1988 | Lukacsko et al. ........... 514/160 |
| 4,758,579 A | 7/1988 | Kohl et al. |
| 4,766,117 A | 8/1988 | Crawford et al. ........... 514/219 |
| 4,786,505 A | 11/1988 | Lovgren et al. ............. 424/468 |
| 4,965,065 A | 10/1990 | Lukacsko et al. ............ 424/10 |
| 5,037,815 A | 8/1991 | Lukacsko et al. ........... 514/162 |
| 5,043,358 A | 8/1991 | Lukacsko et al. ........... 514/653 |
| 5,204,118 A | 4/1993 | Goldman et al. ............ 424/489 |
| 5,260,333 A | 11/1993 | Lukacsko et al. ........... 514/471 |
| 5,364,616 A | 11/1994 | Singer et al. .................. 424/52 |
| 5,373,022 A | 12/1994 | Fawzi et al. ................. 514/570 |
| 5,417,980 A | 5/1995 | Goldman et al. ............ 424/464 |
| 5,466,436 A | 11/1995 | Stables ........................ 514/161 |
| 5,514,663 A | 5/1996 | Mandel .......................... 514/33 |
| 5,631,022 A | 5/1997 | Mandel et al. ............... 424/456 |
| 5,643,960 A | 7/1997 | Breitner et al. .............. 514/570 |
| 5,686,105 A | 11/1997 | Kelm et al. ................... 424/452 |
| 5,716,648 A | 2/1998 | Halskov et al. .............. 424/682 |
| 5,929,030 A | 7/1999 | Hamied et al. |
| 5,932,243 A * | 8/1999 | Fricker et al. ................ 424/450 |
| 5,955,451 A | 9/1999 | Lichtenberger et al. ........ 514/78 |
| 5,965,160 A * | 10/1999 | Benita et al. ................. 424/455 |
| 6,013,281 A | 1/2000 | Lundberg et al. ............ 424/468 |
| 6,025,395 A | 2/2000 | Breitner et al. .............. 514/570 |
| 6,054,136 A | 4/2000 | Farah et al. .................. 424/400 |
| 6,160,020 A | 12/2000 | Ohannesian et al. ........ 514/629 |
| 6,162,816 A | 12/2000 | Bohlin et al. ................ 514/338 |
| 6,207,188 B1 | 3/2001 | Gustavsson et al. ......... 424/464 |
| 6,231,888 B1 | 5/2001 | Lerner et al. ................. 424/463 |
| 6,267,985 B1 | 7/2001 | Chen et al. |
| 6,312,704 B1 * | 11/2001 | Farah et al. .................. 424/401 |
| 6,365,184 B1 | 4/2002 | Depui et al. ................. 424/469 |
| 6,395,298 B1 | 5/2002 | Flanagan et al. ............ 424/479 |
| 6,436,430 B1 * | 8/2002 | Mulye ......................... 424/439 |
| 6,485,747 B1 | 11/2002 | Flanagan et al. ............ 424/479 |
| 6,544,556 B1 | 4/2003 | Chen et al. ................... 424/469 |
| 6,613,354 B2 | 9/2003 | Depui et al. ................. 424/458 |

(Continued)

FOREIGN PATENT DOCUMENTS

DE    4 131 678 A1    10/1992

(Continued)

OTHER PUBLICATIONS

Amidon, et al., "A Theoretical Basis for a Biopharmaceutic Drug Classification: The Correlation of in Vitro Drug Product Dissolution and in Vivo Bioavailability," *Pharm. Res.* 12:413-420 (1995).

(Continued)

*Primary Examiner*—S. Tran
(74) *Attorney, Agent, or Firm*—Arent Fox LLP

(57) ABSTRACT

The present invention claims and discloses a pharmaceutical composition suitable for oral administration, in form of an emulsion pre-concentrate, comprising (i) a compound of formula (I); (ii) one or more surfactants; (iii) optionally an oil or semi-solid fat; said composition forming an in-situ oil-in-water emulsion upon contact with aqueous media such as gastrointestinal fluids. The composition may optionally also comprise one or more short-chain alcohols. The pharmaceutical composition is useful in the treatment of pain and inflammation.

18 Claims, No Drawings

U.S. PATENT DOCUMENTS

| | | | |
|---|---|---|---|
| 6,635,281 B2 * | 10/2003 | Wong et al. | 424/473 |
| 2001/0025107 A1 | 9/2001 | Barberich et al. | 546/273.7 |
| 2001/0036473 A1 | 11/2001 | Scott et al. | 424/463 |
| 2001/0044410 A1 | 11/2001 | Gelber et al. | 514/27 |
| 2002/0012676 A1 | 1/2002 | Lundeberg et al. | 424/400 |
| 2002/0042433 A1 | 4/2002 | Yelle et al. | 514/338 |
| 2002/0044962 A1 | 4/2002 | Cherukuri et al. | 424/459 |
| 2002/0045184 A1 | 4/2002 | Chen | 435/6 |
| 2002/0086029 A1 | 7/2002 | Lundberg et al. | 424/184.1 |
| 2002/0111370 A1 | 8/2002 | Bergman et al. | 514/338 |
| 2002/0155153 A1 | 10/2002 | Depui et al. | 424/452 |
| 2003/0008903 A1 | 1/2003 | Barberich et al. | 514/338 |
| 2003/0113375 A1 | 6/2003 | Lundberg et al. | 424/474 |
| 2003/0129235 A1 | 7/2003 | Chen et al. | 424/470 |
| 2004/0052824 A1 * | 3/2004 | Abou Chacra-Vernet et al. | 424/400 |

FOREIGN PATENT DOCUMENTS

| | | |
|---|---|---|
| EP | 0 005 129 B1 | 10/1979 |
| EP | 0 166 287 A1 | 1/1986 |
| EP | 0 174 726 B1 | 3/1986 |
| EP | 0 274 870 | 7/1988 |
| EP | 0 274 870 A2 * | 7/1988 |
| EP | 0 320 550 A1 | 6/1989 |
| EP | 0 426 479 A1 | 5/1991 |
| EP | 0 426 479 B1 | 5/1991 |
| EP | 0 550 083 B1 | 7/1993 |
| EP | 0 984 012 A2 | 3/2000 |
| GB | 2 105 193 | 3/1983 |
| GB | 2 163 747 A | 3/1986 |
| WO | WO 85/03443 | 8/1985 |
| WO | 90/06925 A1 | 6/1990 |
| WO | WO 93/12817 | 7/1993 |
| WO | WO 94/04484 | 3/1994 |
| WO | WO 94/07541 | 4/1994 |
| WO | WO 94/12463 | 6/1994 |
| WO | 94/27988 A1 | 12/1994 |
| WO | 95/01977 A1 | 1/1995 |
| WO | WO 95/08983 | 4/1995 |
| WO | WO 95/09831 | 4/1995 |
| WO | WO 9509831 A1 * | 4/1995 |
| WO | WO 95/30641 | 11/1995 |
| WO | 96/01623 A1 | 1/1996 |
| WO | 97/25064 A1 | 7/1997 |
| WO | WO 98/22117 | 5/1998 |
| WO | WO 99/00380 | 1/1999 |
| WO | WO 99/12524 | 3/1999 |
| WO | WO 99/56727 | 11/1999 |
| WO | 00/57885 A1 | 10/2000 |
| WO | WO 00/71122 | 11/2000 |
| WO | WO 00/72838 A1 * | 12/2000 |
| WO | 01/66088 A1 | 9/2001 |
| WO | WO 03/017980 A1 | 3/2003 |

OTHER PUBLICATIONS

Burns, et al., "Formulation Strategies Designed to Maintain the Biphasic Release Characteristics of Liquid-Filled Capsules," *Int. J. Pharm.* 141:9-16 (1996).

Shah, et al., "Self-Emulsifying Drug Delivery Systems (SEDDS) with Polyglycolyzed Glycerides for Improving in vitro Dissolution and Oral Absorption of Lipophilic Drugs," *Int. J. Pharm.* 106:15-23 (1994).

English language abstract for AH1 above.

Bowtle, et al., "Liquid Filling of Hard Gelatin Capsules: A New Technology for Alternative Formulations,"*Phar. Tech. Eur.*, Oct. 1998, pp. 84-90.

Cole, "Liquid-Filled Hard-Gelatin Capsules," *Pharm. Tech. Intl.*, Sep./Oct. 1989, pp. 29-33.

Young, "Liquid Fill of Two Piece Hard Shells—A Fluid Solution to Current Problems," *Pharm. Mfg. Packing Sourcer*, Mar. 1999, pp. 14-22.

English language abstract of DE 198 01 811 (reference CK).

Bigard et al., "Complete Prevention by Omeprazole of Aspirin Induced Gastric Lesions in Healthy Subjects," *GUT* 29A712, T49, 1988.

Bombardier et al., "Comparison of Upper Gastrointestinal Toxicity of Rofecoxib and Naproxen in Patients with Rheumatoid Arthritis," *N. Engl. J. Med.* 343 1520-1528, 2000.

Brown et al., "Prevention of the Gastrointestinal Adverse Effects of Nonsteroidal Anti-Inflammatory Drugs," *Prac. Drug Safety* 21 503-512, 1999.

Cullen et al., "Primary Gastroduodenal Prophylaxis with Omeprazole for Non-Steroidal Anti-Inflammatory Drug Users," *Aliment. Pharmacol. Ther.* 12 135-140, 1998.

Dent, "Why Proton Pump Inhibition Should Heal and Protect Against Nonsteroidal Anti-Inflammatory Drug Ulcers," *Am. J. Med.* 104 52S-55S, 1998.

Hawkey, "Progress in Prophylaxis Against Nonsteroidal Anti-Inflammatory Drug-Associated Ulcers and Erosions," *Am. J. Med.* 104 67S-74S, 1998.

Hawkey et al., "Omeprazole Compared with Misoprostol for Ulcers Associated with Nonsteroidal Anti-Inflammatory Drugs," *N. Engl. J. Med.* 338 727-734, 1998.

Howden, "Clinical Pharmacology of Omeprazole," *Clin. Pharmacokinet.* 20 38-49, 1991.

Katz et at, "Gastric Acidity and Acid Breakthrough with Twice-Daily Omeprazole or Iansoprazole," *Aliment. Pharmacol. Ther* 14 709-714, 2000.

Kephart et al., "Coprescribing of nonsteroidal Anti-Inflammatory Drugs and Cytoprotective and Antiulcer Drugs in Nova Scotia's Senior Population," *Clin. Ther.* 17 1159-1173, 1995.

Kimmey et al., "Role of $H_2$-Receptor Blockers in the Prevention of Gastric Injury Resulting from Nonsteroidal Anti-inflammatory Agents," *Am. J. Med.* 84 49-52, 1988.

Lad et al., "Management of Nonsteroidal Anti-Inflammatory Drug-Induced Gastroduodenal Disease by Acid Suppression," *Can. J. Gastroenterol* 13 135-142, 1999.

Lee et al., "Omeprazole Prevents Indomethacin-Induced Gastric Ulcers in Rabbits," *Aliment. Pharmacol. Ther.* 10, 571-576, 1996.

Lichtenberger et al., "Nonsteroidal Anti-Inflammatory Drug and Phospholipid Prodrugs: Combination Therapy with Antisecretory Agents in Rats," *Gastroenterology* 111, 990-995, 1996.

Mattsson et al., "Omeprazole Provides Protection Against Experimentally Induced Gastric Mucosal Lesions," *Eur J. Pharmacol.* 91, 111-114, 1983.

Oddsson et al., "Endoscopic Findings in the Stomach and Duodnum after Treatment with Enteric-Coated and Plain Naproxen Tablets in Healthy Subjects," *Scand. J. Gestroenterol.* 25, 231-234, 1990.

Savarino et al., "Effect of One-Month Treatment with Nonsteroidal Antiinflamatory Drugs (NSAIDs) on Gastric pH of Rheumatoid Arthritis Patients," *Digestive Disease and Sciences* 43, 459-463, 1998.

Scheiman, "NSAID-Induced Peptic Ulcer Disease: A Critical Review of Pathogenesis and Management," *Dig. Dis.* 12, 210-222, 1994.

Selway, "Potential Hazards of Long-Term Acid Suppression," *Scand J. Gastroenterol.* 25 (Supp. 178), 85-92, 1990.

Silverstein et al.,"Gastrointestinal Toxicity with Celecoxib vs. Nonsteroidal Anti-Inflammatory Drugs for Osteoarthritis and Rheumatoid Arthritis; The Class Study: A Randomized Controlled Trial," *JAMA* 284, 1247-1255, 2000.

Tronstad et al., "Gastroscopic Findings after Treatment with Enteric-Coated and Plain Naproxen Tablets in Healthy Subjects," *Scand. J. Gestroenterol.* 20, 239-242 ,1985.

Wagner at al., "Effects of Nonsteroidal Antiinflammatory Drugs on Ulcerogenesis and Gastric Secretion in Pylorus-Ligated Rat," *Digestive Diseases and Sciences* 40, 134-140, 1995.

Wolfe et al., "Gastrointestianal Toxicity of Nonsteroidal Anti-Inflmmatory Drugs," *N. Engl. J. Med.* 340, 1888-1899, 1999.

Yeomans et al., "A Comparison of Omeprazole with Ranitidine for Ulcers Associated with Nonsteroidal Anti-Inflammatory Drugs," *N. Engl. J. Med.* 338, 719-726, 1998.

Yeomans, "New Data on Healing of Nonsteroidal Anit-Inflammatory Drug-Associated Ulcers and Erosioins," *Am. J. Med.* 104, 56S-61S, 1998.

* cited by examiner

SELF EMULSIFYING DRUG DELIVERY SYSTEM

CROSS REFERENCE TO RELATED APPLICATIONS

The present application represents U.S. national stage of international application PCT/SE01/00466, which had an international filing date of Mar. 6, 2001, and which was published in English under PCT Article 21(2) on Sep. 13, 2001. The international application claims priority to Swedish application 0000774-0, filed on Mar. 8, 2000.

FIELD OF THE INVENTION

The present invention is directed to a new pharmaceutical composition in form of an emulsion pre-concentrate, a unit dosage form comprising said composition, its use in therapy as well as a process for the preparation thereof.

BACKGROUND AND PRIOR ART

Non-steroidal anti-inflammatory drugs, commonly abbreviated NSAIDs, are well-known drugs for the treatment of pain and inflammation. One of the major drawbacks with NSAIDs is that they have severe gastro-intestinal side-effects. Patients undergoing treatment with NSAIDs for a longer period of time, such as naproxen, often experience problems with stomach gastrointestinal side-effects.

Nitrogen oxide releasing NSAID compounds (in the following NO-releasing NSAIDs), have recently been found to have an improved side-effect profile, see e.g. WO 94/04484. WO 94/12463, WO 95/09831 and WO 95/30641.

NO-releasing NSAIDs are lipophilic compounds with poor aqueous solubility. They can be classified into class 2 according to the Biopharmaceutical Classification System proposed by Amidon et al. (*Pharm. Res.* 12 (1995) pp. 413-420). Drugs of this class are characterised by low aqueous solubility but reasonably well permeability. A biopharmaceutical problem with these compounds is that their absorption from the gastro-intestinal tract (GIT) may be dissolution rate limited, resulting in poor bioavailability upon oral administration.

WO 95/08983 discloses a self-emulsifying composition for oral administration that forms a microemulsion in situ when in contact with biological fluids. This composition can be characterised as a self-microemulsifying drug delivery system (SMEDDS), and comprises at least
an active compound.
a lipophilic phase consisting of a mixture of glycerides and fatty acid esters.
a surface-active agent.
a cosurfactant, and
a hydrophilic phase which is achieved after ingestion by the physiological liquid of the digestive medium.

The present invention distinguishes in several aspects from WO 95/08983 and other SMEDDS. Whereas the compositions disclosed in WO 95/08983 form a microemulsion in situ, the compositions of the present invention form an emulsion. The SMEDDS of WO 95/08983 require the presence of a lipophilic phase to solubilise the active compound. Such a lipophilic solubiliser phase is not needed for the present invention since the active compound, the NO-releasing NSAID, is able to solely constitute the oil phase of the in situ emulsion. Compositions of WO 95/08983 comprise inter alia a cosurfactant in addition to a surface-active agent. The presence of a cosurfactant is not necessary for compositions of the present invention reducing toxicological concern to a minimum.

EP 274 870 discloses a pharmaceutical composition comprising a non-steroidal anti-inflammatory drug (NSAID) and a surfactant, the composition being capable of forming micelles containing the NSAID upon oral administration. These micelles have been found to present a particularly appropriate form to administer NSAIDs orally, alleviating their adverse effects on the gastrointestinal tract (GIT). Micelles are aggregates in which the surfactant molecules are generally arranged in a spheroidal structure with the hydrophobic region at the core shielded, in an aqueous solution, from the water by a mantle of outer hydrophilic regions. The drug is usually solubilised in the surfactant. Micelles are to be contrasted in terms of their structure with emulsions which are formed by compositions of the present invention. Whereas micelles are thermodynamically stable one-phase-systems (according to the Gibbs phase law) in which the aggregates usually have a diameter of approximately two lengths of the surfactant molecule forming it, i.e. in the order of some ten to hundred Ångström (Å), emulsions are much larger aggregates, in the order of nanometers to micrometers in diameter, consisting of an oily core which is surrounded by one or several layers of surfactants. Emulsions are generally two-phase-systems, and they are thermodynamically unstable (but may be kinetically stable). Another major difference between the compositions of EP 274 870 and the present invention is the nature of the active compound. Whereas NSAIDs are crystalline powders by nature, the NO-releasing NSAIDs or mixtures of NO-releasing NSAIDs used in the present invention are in oil form or a thermosoftening semisolid. Moreover, micelles usually require a much higher drug:surfactant ratio compared to the oil:surfactant ratio required to form an emulsion.

One of the unique features with NO-releasing NSAIDs is that many of these compounds are oils or thermosoftening semisolids which are practically insoluble in water. With high-dose NO-releasing NSAIDs. e.g. when the dose is above about 350 mg, it is difficult to formulate a tablet of reasonable size of the large amount of oil or semisolid. The lipophilic NO-releasing NSAIDs can, however, be formulated as oil-in-water emulsions where the compound constitutes, or is part of, the oil phase emulsified in water by one or more surfactants.

In pharmacokinetic animal studies it has been surprisingly found that such oil-in-water emulsions of NO-releasing NSAIDs display a much better bioavailability compared to the unemulsified substance. A problem with emulsions is, however, that they are thermodynamically unstable and have a poor long-term storage stability since they often tend to coalescence, creaming/sedimentation or phase separation. Moreover, they do not represent a convenient dosage form for oral administration since often large volumes are needed to incorporate one dose, and unpleasant bitter or soapy taste may be a major problem. It is inter alia not possible to fill oil-in-water emulsions into gelatine capsules since the high water content of the emulsion is incompatible with the capsule shell and would dissolve it.

OUTLINE OF THE INVENTION

The problems mentioned above have now been solved by providing a novel Self Emulsifying Drug Delivery System, commonly known as SEDDS, suitable for oral administration. More particularly, the present invention is directed to a pharmaceutical composition suitable for oral administration, in form of an emulsion pre-concentrate, comprising (i) a compound of the formula (I)

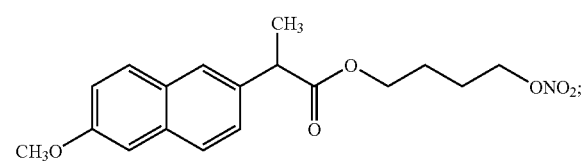

(ii) one or more surfactants;

(iii) optionally an oil or semi-solid fat;

said composition forming an in-situ oil-in-water emulsion upon contact with aqueous media such as gastrointestinal fluids.

The composition according to the present invention may optionally further comprise one or more short-chain alcohols.

The composition will form an in situ oil-in-water emulsion of small droplets of nanometer to micron size upon contact with gastrointestinal fluids, the droplets being constituted of a compound of the formula (I) above, forming the core of the droplet which is covered by one or several layers of surfactant. The in situ formed oil-in-water emulsion will provide a good bioavailability of the compound of the formula (I) upon oral administration. Storage stability of the emulsion is not a concern since the emulsion is not formed until the pre-concentrate has been taken by the patient, i.e. first at the moment of administration. The possibly unpleasant taste of the pre-concentrate is not a problem when filled into capsules.

The pharmaceutical composition according to the present invention is an emulsion pre-concentrate at the time of administration to a patient. The emulsion pre-concentrate can be filled into single unit dosage forms such as capsules, drinking ampoules and dose cushions, or may alternatively be formed as other suitable dosage forms such as chewable soft pills and chewy-base lozenges.

Upon contact with aqueous media such as gastrointestinal fluids, the emulsion pre-concentrate transforms into an oil-in-water emulsion. Thus, the composition will form an in-situ oil-in-water emulsion in the gastrointestinal tract (GI tract). The drug release rate of the composition is determined by the droplet size of the in situ emulsion and the polarity of the emulsion droplets, the latter being governed by the hydrophilic-lipophilic balance (HLB) of the drug/surfactant mixture, and the concentration of the surfactant. Generally, small droplet size and high polarity gives rise to a high drug release rate (N. H. Shah et al., *Int. J. Pharm.* 106 (1994), pp. 15-23)

The compound of the formula (I) above consists of naproxen, a butyl spacer and a NO-releasing moiety, said three parts being linked together into one single molecule. Naproxen is by nature in form of a powder, whereas NO-releasing naproxen of the formula (I) above provides a compound in oil form as such at room temperature, due to the spacer. This unique feature provides the advantage that no external lipophilic oil or semisolid matrix needs to be added to the emulsion pre-concentrate, since this is an inherent feature of the drug. Additionally, a pharmacologically inert oil or semisolid fat may be added to the pharmaceutical composition by means of a filler or as a viscosity regulator. A filling agent may be required to increase dosing accuracy for low doses. A viscosity regulator may be required in order to adjust optimal viscosity for filling of the composition into e.g. capsules. In particular high speed liquid filling of capsules requires careful adjustment of viscosity within a range that prevents splashing on the low viscosity end and thread formation on the high viscosity end. Moreover, the viscosity range must be chosen so as to give a pumpable formulation. The viscosity range typically required for liquid filling of capsules is from 0.1 to 25 Pa s.

The total amount of the compound of the formula (I) used in the composition of the invention is preferably in the range 50-1500 mg per unit dose. In still a further preferred embodiment, the amount of the compound of the formula (I) used in the composition is 125-500 mg per unit dose.

The wording "unit dose" is defined as the amount of active compound administered in one single capsule, or dissolved in one glass of water.

The wording "surfactant" is defined as surface-active amphiphilic compounds such as block co-polymers. Preferred surfactants in accordance with the present invention are non-ionic surfactants, for example those containing polyethylene glycol (PEG) chains, particularly block co-polymers such as poloxamers.

Examples of suitable poloxamers are Poloxamer 407 (Pluronic F127®); Poloxamer 401 (Pluronic L121®); Poloxamer 237 (Pluronic F87®); Poloxamer 338 (Pluronic F138®); Poloxamer 331 (Pluronic L101®); Poloxamer 231 (Pluronic L81®); tetrafunctional polyoxyethylene polyoxypropylene block copolymer of ethylene diamine, known as Poloxamine 908 (Tetronic 908®); Poloxamine 1307 (Tetronic 1307®); Poloxamine 1107 polyoxyethylene polyoxybutylene block copolymer, known as Polyglycol BM45®. This list is only intended to serve as exemplification of surfactants that may be used in accordance with the present invention, and should not in any way be considered as exhaustive or as limiting the invention.

All surfactants described above are commercially available from e.g. BASF, Dow Chemicals, and Gattefossé.

The total amount of surfactant(s) in accordance with the invention may be within the range of from 12.5-6000 mg, preferably of from 100-500 mg. The ratio NO-releasing NSAID:surfactant may vary from 1:0.1 to 1:10, preferably from 1:0.3 to 1:3.

If an additional oil is added to the pharmaceutical composition this may be any oil as long as it is inert and compatible with the capsule material, as well as being acceptable for use in pharmaceuticals. A person skilled in the art will appreciate which oil to select for the intended purpose. Examples of suitable oils that may be used in accordance with the present invention are vegetable oils such as coconut oil, corn oil, soybean oil, rapeseed oil, safflower oil, and castor oil. Also animalic oils such as fish oil and triglycerides are suitable for the purposes of the present invention.

If a semi-solid fat is used as a filler for the pharmaceutical composition, this may preferably be selected from mono-, di- and triglycerides, fatty acid alcohols such as stearyl alcohol, Gelucires 33/01®, 39/01®, 43/01®, glyceryl palmitostearate such as Precirol ATO5®. Gelucire is a mixture obtained by mixing mono-, di-, and tri-esters of glycerol, mono- and di-esters of PEG, or free PEG.

If an oil or semi-solid fat is used in the pharmaceutical composition according to the invention, this may serve as a filler or as a viscosity regulator.

The wording "short-chain alcohols" used in accordance with the present invention is herein defined as linear or branched mono-, di- or tri-alcohols having 1-6 carbon atoms. Examples of such short-chain alcohols useful in accordance with the invention are ethanol, propylene glycol and glycerol.

If a short-chain alcohol is added to the pharmaceutical composition according to the invention, the solubility is enhanced and a smaller amount of surfactant is required.

The pharmaceutical composition of the invention is filled into single dosage forms suitable for oral administration, such as capsules, drinking ampoules and dose cushions, or may be formulated as other suitable oral dosage forms such as chewable soft pills and chewy-base lozenges.

In a preferred embodiment of the invention, the pharmaceutical composition is filled into hard gelatin capsules, but capsules from alternative materials such as methylcellulose-based shells, and soft gelatine capsules may also be used.

In an alternative embodiment of the invention, the pharmaceutical composition may be dissolved in e.g. a glass of water, thus allowing the pre-concentrate to form an emulsion which may be taken as an oral solution. The compositions intended for dissolution prior to administration may be filled e.g. into soft gelatine capsules, plastic or aluminium cushions, or plastic or glass ampoules. This feature is particularly advantageous for high dose compositions which would require a large capsule, for patients who have difficulty in swallowing capsules, and for pediatric patients.

In a preferred embodiment the pharmaceutical composition of the present invention is filled into capsules. Preferred capsules are gelatin capsules which may be soft or hard. The hard gelatine capsule consists of two pieces, a cap and a body, one fitting inside the other. The hard gelatine capsules are produced empty and filled in a separate operation step. The soft gelatin capsule is a capsule which is manufactured and filled in one single operation.

As mentioned above, the emulsion pre-concentrate transforms into an oil-in-water emulsion upon contact with the gastrointestinal fluids, whereby the active drug is released. Thus, the composition will form an in situ oil-in-water emulsion in the gastrointestinal tract (GI tract).

The pharmaceutical composition of the present invention is particularly useful in the treatment of pain and inflammation. The wording "pain" is intended to include, but not limited to, nociceptive and neuropathic pain or combinations thereof, acute, intermittent and chronic pain; cancer pain; migraine and headaches of similar origin. The wording "inflammation" is intended to include, but not limited to, rheumatoid arthritis; ostheoarthritis; and juvenile arthritis.

Methods of Preparation

The pharmaceutical composition of the present invention may be prepared mainly by the following alternative methods:

I. Mixing

Ia) The oily compound of the formula (I) is put in a vessel, solid surfactant and solid/oily fat (optional) is added. The mixture is heated to the temperature corresponding to the melting point of the excipients, making the formulation fluid, mixed thoroughly until homogenous (visual inspection) and the pre-concentrate is filled into capsules suitable for oral administration.

Ib) Alternatively, the oily compound of the formula (I) is put in a vessel and fluid surfactant is added. The mixture is mixed thoroughly until homogenous (visual inspection) and the pre-concentrate is filled into capsules suitable for oral administration.

c) In a further alternative method, the oily compound of the formula (I) is put in a vessel, finely grinded (particle size <177 um) solid surfactant is added. The liquid mixture is mixed thoroughly until homogenous (visual inspection) and the pre-concentrate is filled into capsules suitable for oral administration.

Id) In still an alternative method the semi-solid/solid surfactant (s) is put in a vessel, and one or more alcohols are added. The mixture is heated to the temperature corresponding to the melting point of the excipients, making the formulation fluid, mixed thoroughly until homogenous (visual inspection). The oily compound of the formula (I) is added, and the mixture is mixed thoroughly until homogenous (visual inspection). The pre-concentrate is filled into capsules suitable for oral administration.

Ie) In yet a further alternative method the liquid surfactant(s) is put in a vessel, and one or more alcohols are added. The mixture is blended thoroughly until homogenous (visual inspection). The oily compound of the formula (I) is added, and the mixture is mixed thoroughly until homogenous (visual inspection). The pre-concentrate is filled into capsules suitable for oral administration In order to fill a two-piece capsule or a softgel capsule with a liquid, the formulation must be within a certain viscosity range, as determined by the manufacturer, at the filling temperature suitable for the process. For a two-piece capsule the maximum filling temperature is roughly 70° C. The viscosity of the formulation should normally be in the range 50-1000 cPoise (=0.05-1 Pas) at the temperature chosen for the filling process. For the filling of the formulation into softgel capsules, process temperature is not allowed to exceed 30-40° C. (the exact temperature depending on the manufacturer). The formulation must be liquid and have a viscosity that allows it to be pumpable at the filling temperature. In order to make the formulation liquid with an acceptable viscosity, several additives may be used, for example Cremophor EL®.

II. Filling

For the filling procedure it is required that the composition is in liquid form at the temperature of filling. Semisolid thermosoftening compositions are therefore filled above the liquifying, temperature. Soft gelatine capsules are manufactured and filled in one operation, and may be filled at temperatures of up to 40° C., whereas hard gelatine capsules may be filled at temperatures of up to 70° C. Hard gelatin capsules filled with compositions that remain liquid at storage temperature require sealing, e.g. by gelatin banding, to prevent leakage. The process of liquid filling of hard gelatin capsules and product requirements are e.g. described in W. J. Bowtle. *Pharmaceutical Technology Europe*, October 1998: V. M. Young, *Pharmaceutical Manufacturing and Packaging Sourcer*, March 1999: and E. T Coole. *Pharmaceutical Technology International*. September/October 1989. Using two piece capsules permits filling of more than one phase into a single capsule, which may be desired for bi- or multiphase drug release (W. J Bowtle et al., *Int. J. Pharm.* 141 (1996), pp 9-16). Several phases of solidifying material can be filled in single steps. The final phase may be liquid if required. The number of phases is only restricted by the capsule size, and volume of the single phases. This special feature may also allow controlled release or separation of different drug substances formulated in the same capsule. Additionally, capsules may be processed further. e.g. by enteric coating.

III. Characterisation of the Formulations

In order to characterise formulations, the time required for the formulation to form an oil-in-water emulsion upon contact with simulated gastric fluid. SGF, (without enzymes), is determined, and the formed emulsion is characterised. SGF comprises of 7 milliliters concentrated hydrochloric acid, 2 grams of sodium chloride and distilled water to give the solution a total volume of 1 L. The "emulsion forming test" is performed in test tubes (beaker) with magnetic stirring. The test tube, containing a small magnet, is filled with 12.5 ml SGF without enzymes, corresponding to one tenth of the average volume of gastric fluid in humans, and formulation corresponding to one tenth of the dose of the active compound of formula (I) is added.

The time for emulsion formation will vary from 30 seconds and up to 15 minutes, depending on the composition of the formulation. If one or more short-chain alcohols are added, the time for emulsion formation will vary between 2-3 seconds and 3-4 minutes. Also the average particle size of the formed emulsion is studied with Laser Diffraction, LD, or Photon Correlation Spectroscopy, PCS. Depending on particle size either of the two methods may be used.

DETAILED DESCRIPTION OF THE INVENTION

The invention will now be described in more detail by the following examples, which are not to be construed as limiting the invention.

The following emulsion pre-concentrates were prepared.

Example 1

|  | amount [g] |
|---|---|
| (i) Compound of formula (I) | 1000 |
| (ii) Pluronic F127 ® | 1000 |

A semi-solid formulation was obtained by melting 1 kg of Pluronic F127® (Poloxamer 407) by heating to 62° C. The melt was stirred thoroughly to ensure that no solid particles were present. 1 kg of the compound of formula (I) was added to the melted Pluronic F127®, and the mixture was allowed to reach a temperature of 62° C. The liquid formulation was mixed until homogenous (checked by visual inspection). The resulting liquid formulation was then filled into hard gelatin capsules. The formulation becomes a semi-solid upon cooling (in the capsule).

Characterization 150 milligram of the formulation was put in 12.5 milliliters of SGF (without enzymes) and magnetic stirring. The following results were obtained:

| Time to emulsion: | 13 minutes |
|---|---|
| Average particle size: | 2-3 μm |

The viscosity was measured in a Stress Tech cone and plate viscometer, measurement system C 40 4 PC, at the shear rate 20 $s^{-1}$. The flow was more or less Newtonian.

Example 2

|  | amount [g] |
|---|---|
| (i) Compound of formula (I) | 1000 |
| (ii) Pluronic L121 ® | 1000 |

A liquid formulation was prepared by mixing 1 kg of the liquid surfactant Poloxamer 401, with 1 kg of the compound of formula (I) at room temperature. The liquid formulation was mixed until homogenous (checked by visual inspection). The resulting liquid formulation was then filled into hard gelatin capsules.

Characterization 150 milligram of the formulation was put in 12.5 milliliters of SGF (without enzymes) and magnetic stirring. The following results were obtained:

| Time to emulsion: | 20 seconds |
|---|---|
| Average particle size: | 11 μm |

Example 3

|  | amount [g] |
|---|---|
| (i) Compound of formula (I) | 1000 |
| (ii) Polyglycol BM 45 ® | 1000 |
| (iii) Sodium dodecyl sulphate | 40 |

A formulation was obtained by mixing 1 kg of Polyglycol BM 45® (Poloxamine 1107), 40 grams of sodium dodecyl sulphate, acting as a co-surfactant, and 1 kg of the compound of formula (I). The liquid formulation was mixed until homogenous (checked by visual inspection). The resulting liquid formulation was then filled into hard gelatin capsules.

Characterization 150 milligram of the formulation was put in 12.5 milliliters of SGF (without enzymes) and magnetic stirring The following results were obtained:

| Time to emulsion: | 15 minutes |
|---|---|
| Average particle size: | 0.7 μm |

Example 4

|  | amount [g] |
|---|---|
| (i) Compound of formula (I) | 1000 |
| (ii) Pluronic F127 ® | 500 |
| (iii) Cremophor EL ® | 500 |

To be able to fill the semi-solid formulation into soft gelatin capsules, process temperatures must be below 30-40° C. (the specific temperature depends on manufacturer). This means that the formulation must be fluid and pumpable below 30-40° C. To obtain a formulation fluid at this temperature, some of the surfactant was replaced with Cremophor EL®. A melt was prepared as described in Example 1, except for the substitution of 0.5 kg surfactant with the same amount of Cremophor EL®.

Characterization 150 milligram of the formulation was put in 12.5 milliliters of SGF (without enzymes) and magnetic stirring. The following results were obtained:

| | |
|---|---|
| Time to emulsion: | 9 minutes |
| Average particle size: | 4-5 µm |

Example 5

| | amount [g] |
|---|---|
| (i) Compound of formula (I) | 1250 |
| (ii) Pluronic F127 ® | 1500 |
| (iii) Fractionated coconut oil | 1880 |

To ensure that low dose formulations will have a good filling precision, and to fill a capsule of a certain volume to minimise the amount of air present, the active compound may be filled up to volume with aliquot part coconut oil. A semi-solid formulation was obtained by melting 1.500 kg of Pluronic F127® (Poloxamer 407) by heating to 62° C. The melt was stirred thoroughly to ensure that no solid particles were present. 1.250 kg of the compound of formula (I) and 1.880 kg of fractionated coconut oil were added to the melted Pluronic F127®, and the mixture was allowed to reach a temperature of 62° C. The liquid formulation was mixed until homogenous (checked by visual inspection). The resulting liquid formulation was then filled into hard gelatin capsules.

Characterization

One tenth of the formulation was put in 12.5 milliliters of SGF (without enzymes) and magnetic stirring. The following results were obtained:

| | |
|---|---|
| Time to form emulsion: | 10 minutes |
| Average particle size: | 5 µm |

Example 6

| | amount [g] |
|---|---|
| (i) Compound of formula (I) | 62.5 |
| (ii) Poloxamer 407 | 375 |
| (iii) Fractionated coconut oil | 312.5 |

The formulation was prepared as described for Example 5 above.

Characterization

Characterization was performed as for Example 5 above. The following results were obtained:

| | |
|---|---|
| Time to form emulsion: | 10 minutes |
| Average particle size: | 36 µm |

Example 7

| | amount [g] |
|---|---|
| (i) Compound of formula (I) | 62.5 |
| (ii) Poloxamer 407 ® | 375 |
| (iii) Fractionated castor oil | 312.5 |

The formulation was prepared as described for Examples 5 above.

Characterization

Characterization was performed as for Example 5 above. The following results were obtained:

| | |
|---|---|
| Time to form emulsion: | 10 minutes |
| Average particle size: | 81 µm |

Example 8

| | amount [g] |
|---|---|
| (i) Compound of formula (I) | 3 |
| (ii) Pluronic L127 ® | 0.843 |
| (iii) sorbitanmonolaurat | 0.282 |
| (iv) glycerol | 0.375 |

A semi-solid formulation was obtained by melting 0.843 gram of Pluronic F127® (Poloxamer 407), 0.282 gram of sorbitanmonolaurat and 0.375 gram of glycerol by heating to 62° C. The melt was stirred thoroughly to ensure that no solid particles were present. 3 Grams of the compound of formula (I) was added to the mixture. The mixture was allowed to reach a temperature of 62° C. The liquid formulation was mixed until homogenous (checked by visual inspection). The resulting liquid formulation was allowed to cool to a temperature of 30° C. and was then filled into soft gelatin capsules. The formulation becomes a semi-solid upon cooling (in the capsule).

Characterization 112 milligram of the formulation was put in 12.5 milliliters of SGF (without enzymes) and magnetic stirring. The following result was obtained:

Time to emulsion: 2.5-3.5 minutes

Example 9

| | amount [g] |
|---|---|
| (i) Compound of formula (I) | 3 |
| (ii) Pluronic L127 ® | 0.843 |
| (iii) sorbitanmonolaurat | 0.282 |
| (iv) propylene glycol | 0.375 |

A semi-solid formulation was obtained by melting 0.843 gram of Pluronic F127® (Poloxamer 407), 0.282 gram of sorbitanmonolaurat and 0.375 gram of propylene glycol by heating to 62° C. The melt was stirred thoroughly to ensure that no solid particles were present. 3 Grams of the compound of formula (I) was added to the mixture. The mixture was allowed to reach a temperature of 62° C. The liquid formulation was mixed until homogenous (checked by visual inspection). The resulting liquid formulation was allowed to cool to a temperature of 30° C., and was then filled into soft gelatin capsules. The formulation stays liquid upon cooling (in the capsule).

Characterization 112 milligram of the formulation was put in 12.5 milliliters of SGF (without enzymes) and magnetic stirring. The following result was obtained:

Time to emulsion: within 20 seconds

Example 10

|   | amount [g] |
|---|---|
| (i) Compound of formula (I) | 3 |
| (ii) Pluronic L101 ® | 0.506 |
| (iii) sorbitanmonolaurat | 0.169 |
| (iv) ethanol | 0.225 |

A liquid formulation was prepared. A solution of 0.506 gram of Pluronic L101® (Poloxamer 331), 0.169 gram of sorbitanmonolaurat and 0.225 gram of ethanol was mixed until homogenous (checked by visual inspection). 3 Grams of the compound of formula (I) was added to the mixture, at room temperature. The resulting liquid formulation was then filled into soft gelatin capsules.

Characterization 97 milligram of the formulation was put in 12.5 milliliters of SGF (without enzymes) and magnetic stirring. The following result was obtained:

Time to emulsion: within 20 seconds

In Vivo Study of Formulations in Mini Pigs

A bioavailability study of formulations according to the present invention was performed after oral administration in fastened minipigs.

6 male Göttingen SPF minipigs were used in the study. At the start of the acclimatization period, the animals were 4 months old and had a weight of from 7.7 to 10.1. kg. The animals were fasted for 12 hours before treatment and until the blood sample at 4 hours post treatment had been taken. A supply of autoclaved hay was given daily as well. Twice daily, the animals were offered domestic quality drinking water.

A pharmaceutical composition of the invention, filled in a suitable unit dosage form according to the invention, was administered to each animal. The dose levels were approximately 15 µmol/kg body weight. 10 ml of tap water was given to facilitate the swallowing of the capsule or corresponding unit dosage.

All visible signs of ill health and any behavioural changes were recorded daily. Any deviation from normal was recorded with respect to time of onset, duration and severity. Included in the daily health check were observations of the consistency of faeces. All animals were weighed on arrival and of the first day of of each treatment.

Blood samples (5 ml) were taken from the jugular vein into Vacutainer tubes containing heparin. Blood samples were taken before treatment (0) and at 15, 30 and 45 minutes; 1, 1.5, 2, 4, 7 and 24 hours after treatment.

The invention claimed is:

1. An emulsion pre-concentrate suitable for oral administration, consisting essentially of:
   (i) a compound of the formula (I)

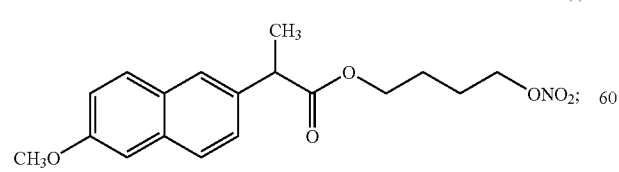

(ii) one or more non-ionic surfactants, wherein the ratio of compound of formula (I):surfactant is within the range of from 1:0.3-1:3; and
   (iii) optionally one or more short-chain alcohols in an amount of about 6% w/w to about 8% w/w,
   wherein said emulsion pre-concentrate forms an in situ oil-in-water emulsion upon contact with aqueous media.

2. The emulsion pre-concentrate according to claim 1, wherein the amount of the compound of formula (I) is from 50-1500 mg per unit dose.

3. The emulsion pre-concentrate according to claim 2, wherein the amount of the compound of formula (I) is 125-500 mg per unit dose.

4. The emulsion pre-concentrate according to claim 1, wherein the non-ionic surfactant is a block co-polymer.

5. The emulsion pre-concentrate according to claim 1, wherein the non-ionic surfactant is a poloxamer.

6. The emulsion pre-concentrate according to claim 5, wherein the non-ionic surfactant is selected from the group consisting of Poloxamer 407; Poloxamer 401; Poloxamer 237; Poloxamer 338; Poloxamer 331; Poloxamer 231; Poloxamine 908; Poloxamine 1307; Poloxamine 1107; and polyoxyethylene polyoxybutylene block copolymer.

7. The emulsion pre-concentrate according to claim 1, wherein the total amount of surfactant(s) is from 12.5-6000 mg.

8. The emulsion pre-concentrate according to claim 7, wherein the total amount of surfactant(s) is from 100-500 mg.

9. The emulsion pre-concentrate according to claim 1, wherein the short-chain alcohol is selected from the group consisting of ethanol, propyleneglycol and glycerol.

10. A unit dosage form filled with an emulsion pre-concentrate according to claim 1.

11. A unit dosage form according to claim 10, selected from the group consisting of capsules, drinking ampoules, dose cushion, chewable soft pill, and chewy-base lozenges.

12. A unit dosage form according to claim 11, in the form of a capsule.

13. A unit dosage form according to claim 12, wherein said capsule is a hard gelatine capsule.

14. A unit dosage form according to claim 12, wherein said capsule is a soft gelatine capsule.

15. An oral solution comprising an emulsion pre-concentrate according to claim 1 dissolved in water.

16. A method for the treatment of pain comprising administering an emulsion pre-concentrate according to claim 1, to a patient in need thereof.

17. A method for the treatment of inflammation comprising administering an emulsion pre-concentrate according to claim 1, to a patient in need thereof.

18. An emulsion pre-concentrate suitable for oral administration consisting essentially of:
   (i) a compound of the formula (I)

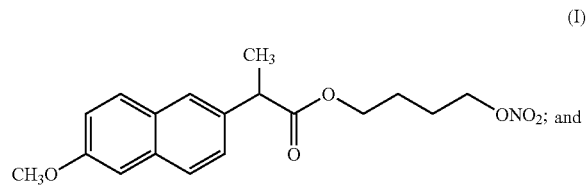

and
   (ii) one or more non-ionic surfactants, wherein the ratio of compound of formula (I):surfactant is within the range of from 1:0.3-1:3,
   wherein said emulsion pre-concentrate forms an in situ oil-in-water emulsion upon contact with aqueous media.

* * * * *